United States Patent
Shu et al.

(10) Patent No.: US 11,191,472 B2
(45) Date of Patent: Dec. 7, 2021

(54) SWEAT ABSORBING TEXTILE ELECTRODE

(71) Applicant: South China University of Technology, Guangdong (CN)

(72) Inventors: Lin Shu, Guangdong (CN); Xiangmin Xu, Guangdong (CN); Can Chen, Guangdong (CN); Tianyuan Xu, Guangdong (CN)

(73) Assignee: South China University of Technology, Guangdong (CN)

( * ) Notice: Subject to any disclaimer, the term of this patent is extended or adjusted under 35 U.S.C. 154(b) by 243 days.

(21) Appl. No.: 16/490,505

(22) PCT Filed: Nov. 20, 2017

(86) PCT No.: PCT/CN2017/111894
§ 371 (c)(1),
(2) Date: Aug. 30, 2019

(87) PCT Pub. No.: WO2019/000808
PCT Pub. Date: Jan. 3, 2019

(65) Prior Publication Data
US 2020/0046246 A1    Feb. 13, 2020

(30) Foreign Application Priority Data
Jun. 30, 2017   (CN) .......................... 201710527136.1

(51) Int. Cl.
*B32B 5/24* (2006.01)
*B32B 7/12* (2006.01)
(Continued)

(52) U.S. Cl.
CPC ............ *A61B 5/291* (2021.01); *A61B 5/6814* (2013.01); *A61B 5/6824* (2013.01);
(Continued)

(58) Field of Classification Search
CPC ........... B32B 7/025; B32B 7/12; B32B 5/245; B32B 15/049; B32B 15/14; A61B 5/25;
(Continued)

(56) References Cited

U.S. PATENT DOCUMENTS 4,088,133 A * 5/1978 Twentier ................ A61B 18/16
600/384
5,499,628 A   3/1996 Wright
(Continued)

FOREIGN PATENT DOCUMENTS

CN   202654120 U    1/2013
CN   204394465 U    6/2015
(Continued)

OTHER PUBLICATIONS

WIPO, Chinese International Search Authority, International Search Report and Written Opinion dated Mar. 28, 2018 in International Patent Application No. PCT/CN2017/111894, 10 pages.

*Primary Examiner* — Michael Zhang
(74) *Attorney, Agent, or Firm* — Masuvalley & Partners

(57) ABSTRACT

A novel sweat absorbing textile electrode comprises a textile electrode body and an electrical coupling member, the textile electrode body comprising a conductive foam and a conductive fabric wrapped around the conductive foam, the electrical coupling member being fixed on the conductive fabric; wherein a through hole is provided on the conductive fabric on the side in contact with the human skin. The textile electrode has a light weight, small size and soft texture. It fits on the skin, has good air permeability, and is capable to absorb sweat, which can prevent short circuit between electrodes caused by sweat and be used for collecting bioelectrical signal when sweat comes out from human
(Continued)

body. It may also be applied in bioelectrical signal monitoring in high temperature, high humidity environment, and during daily exercise.

9 Claims, 1 Drawing Sheet

(51) Int. Cl.
    *B32B 15/04*     (2006.01)
    *B32B 15/14*     (2006.01)
    *B32B 7/025*     (2019.01)
    *A61B 5/291*     (2021.01)
    *A61B 5/00*     (2006.01)

(52) U.S. Cl.
    CPC ........ *A61B 2562/0215* (2017.08); *B32B 5/245* (2013.01); *B32B 7/025* (2019.01); *B32B 7/12* (2013.01); *B32B 15/046* (2013.01); *B32B 15/14* (2013.01); *B32B 2307/202* (2013.01); *B32B 2535/00* (2013.01)

(58) Field of Classification Search
    CPC .............. A61B 5/0531; A61B 2562/14; A61B 2562/182; A61B 2562/164; A61B 2562/0215

See application file for complete search history.

(56) References Cited

U.S. PATENT DOCUMENTS

| | | | | |
|---|---|---|---|---|
| 5,928,142 A | * | 7/1999 | Cartmell | ................ A61B 5/274 600/372 |
| 2012/0046535 A1 | * | 2/2012 | Lin | .......................... A61B 5/25 600/396 |
| 2014/0213882 A1 | * | 7/2014 | Chung | ................ A61B 5/0006 600/395 |

FOREIGN PATENT DOCUMENTS

| | | | | |
|---|---|---|---|---|
| CN | 204500682 U | | 7/2015 | |
| CN | 106551693 A | | 4/2017 | |
| CN | 107198519 A | | 9/2017 | |
| WO | WO-2014204323 A1 | * | 12/2014 | ........... D03D 1/0088 |

* cited by examiner

SWEAT ABSORBING TEXTILE ELECTRODE

RELATED APPLICATIONS

This application is the U.S. National Phase of and claims priority to International Patent Application No. PCT/CN2017/111894, International Filing Date Nov. 20, 2017, entitled New Sweat-Absorbent Fabric Electrode; which claims benefit of Chinese Application No. 201710527136.1 filed Jun. 30, 2017; both of which are incorporated herein by reference in their entireties.

TECHNICAL FIELD

The present invention relates to wearable electronics and sensor technology, and more particularly to a textile electrode for collecting bioelectrical signals.

BACKGROUND ART

With the development of science and technology, people's attention to physical and mental health is increasing. Various bioelectrical signals from human body, such as EEG, ECG, and EMG, can reflect the physiological or psychological characteristics of a human. Through certain signal collecting methods, these signals from human body are collected, analyzed and processed, where effective body information can be obtained, thereby analyzing the health or emotion of a human.

An electrode is a medium directly connecting a signal collection device to the human skin. The quality of the contact with the human skin and the magnitude of the contact resistance greatly affect the quality of signal collection. When multi-site bioelectrical signal monitoring is carried out under conditions like exercise, hot weather, high temperature and high humidity, etc., sweat on forehead, arms and other areas could easily lead to short circuit between electrodes because of the conductivity of moisture and NaCl electrolyte in the sweat. Under this circumstance, the performance of a conventional wet electrode or some conductive silica dry electrodes will be affected. Therefore, in order to realize dynamic monitoring of human bioelectrical signals under exercise or sun exposure condition, an electrode that can effectively absorb sweat is needed.

SUMMARY OF THE INVENTION

In order to solve the technical problems existing in the prior art, the present invention provides a sweat absorbing textile electrode which can quickly and effectively absorb sweat from human body, thereby avoiding short circuit between electrodes in areas with sweat. It can be used for monitoring bioelectrical signals in areas with less or no hair.

The technical solutions of the present invention to solve the above problems are as follows:

A novel sweat absorbing textile electrode comprises a textile electrode body and an electrical coupling member, the textile electrode body comprising a conductive foam and a conductive fabric wrapped around the conductive foam, the electrical coupling member being fixed on the conductive fabric; wherein a through hole is provided on the conductive fabric on the side in contact with the human skin.

Preferably, the textile electrode body further comprises a sweat absorbing layer between the conductive foam and the conductive fabric.

Compared with the prior art, the present invention has the following beneficial effects:

1. The textile electrode of the invention is provided with a conductive foam wrapped by a conductive fabric. The texture thereof is soft, light, comfortable, elastic. It may withstand a certain pressure, exhibit good electrical conductivity and low contact resistance, and be closely attached to the skin.

2. Since the foam is highly water absorptive, the present invention applies the conductive foam in collection of bioelectric signals in areas with lots of sweat. NaCl (300 mg/100 ml) contained in sweat is a strong electrolyte which makes sweat highly electrical conductive. When sweat is immersed in the conductive foam, the conductive foam is filled with the NaCl solution so that the conductivity of the electrode is remarkably enhanced, the skin-electrode resistance is lowered, signal collection is improved, and short circuit or crosstalk between the electrodes due to sweat is avoided.

3. The electrode of the invention has simple structure and low cost, and is suitable for monitoring bioelectrical signals in multiple areas such as forehead and arms.

BRIEF DESCRIPTION OF THE DRAWINGS

FIGS. 1A, 1B and 1C are schematic structural views of an embodiment of the present invention, wherein FIG. 1A is a front view of the electrode, FIG. 1B is a side view of the electrode, and FIG. 1C is a rear view of the electrode;

DETAILED DESCRIPTION OF THE EMBODIMENTS

The present invention will be described in detail below with reference to the drawings and embodiments, but the embodiments of the present invention are not limited thereto.

Example

Figure 1A:
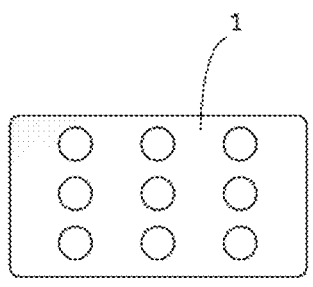
Figure 1B:
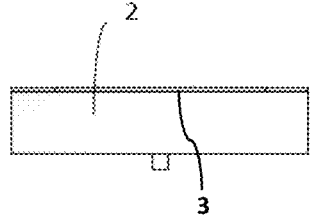
Figure 1C:
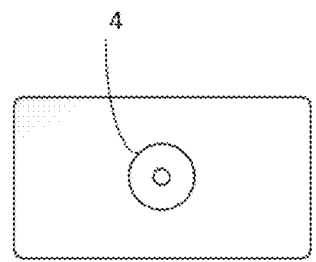

As shown in FIGS. 1A, 1B and 1C, the sweat absorbing textile electrode of the present invention comprises a textile electrode body and an electrical coupling member 4, wherein the textile electrode body comprises a conductive fabric 1, a conductive foam 2 and a sweat absorbing layer 3. The conductive fabric 1 is wrapped around the conductive foam 2 and the sweat absorbing layer 3 to be an outer layer. The sweat absorbing layer is located between the conductive foam and the conductive fabric, which together constitute the textile electrode body. The electrical coupling member is a metal conductive snap 4 attached to the conductive fabric 1 for connection to a signal collection device.

The conductive fabric is formed by plating a metal-based material or coating a layer of conductive material on a cloth. The metal-based material may be selected from gold, silver, nickel or copper, and the conductive material may be selected from graphene or PEDOT. The conductive foam is made from a polymer composite material by foaming, which is made electrically conductive by PVD and exhibit outstanding conductivity. The conductive foam is a cuboid or has other shape with a thickness of 3 mm-8 mm and an adjustable area derived from length*width. The sweat absorbing layer is a cloth that absorbs sweat and is either a conductive fabric or an insulating cloth. Since the conductive foam itself may absorb sweat, the sweat absorbing layer is not essential in the technical solution of the present invention, but is preferable; if there is no sweat absorbing layer, the electrode body comprises only the conductive fabric and the conductive foam.

An adhesive layer is provided on the inner surface of the conductive fabric for bonding the conductive fabric, the conductive foam and the sweat absorbing layer. The adhesive layer may be a conductive adhesive layer or other types of adhesive layer. The fixed connection between the conductive fabric, the conductive foam and the sweat absorbing layer can also be achieved through a conductive wire.

Figure 2:
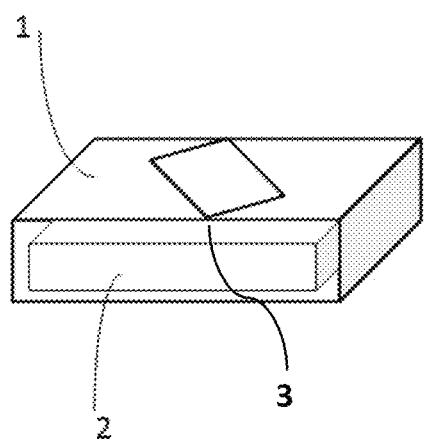
FIG. 2 is a schematic structural view of an electrode according to another embodiment of the present invention.

In order to achieve better ventilation and sweat absorption of the textile electrode, the present invention provides a plurality of through holes on the conductive fabric which is in contact with the human skin, so that the skin can directly contact the sweat absorbing layer or the conductive foam; the through holes can be round or have other shapes. The present invention can also provide a large prismatic through hole directly on the conductive fabric as shown in FIG. 2, so that the sweat absorbing layer contacts with the skin through the prismatic hole more sufficiently. The textile electrode of the structure shown in FIG. 2 has a concentrated sweat absorbing area and exhibits good sweat absorbing performance. In the through holes as shown in FIG. 1A or FIG. 2, a conductive cloth having a weaving density smaller than that of the conductive fabric is further provided. Due to the small weaving density, the sweat absorption by the conductive foam is accelerated, and thus the conductive cloth may achieve a similar effect to the through hole.

The electrical coupling member is a metal conductive snap, and the metal material is gold, silver, copper or platinum. The electrical coupling member can be fixedly connected to the textile electrode body by riveting through the snap.

The resistance of the material can be calculated by the resistance formula $R=\rho L/S$, where $\rho$ is the resistivity of the material, L is the length of the material, and S is the cross-sectional area of the material. The cross-sectional area S of the textile electrode body in the present invention should be the area of the surface parallel to the surface in contact with the skin, and the length L is the thickness of the textile electrode body. Therefore, in view of the internal resistance of the electrode, the conductive foam of the textile electrode body should not be too thick, and the surface area in contact with the skin should be as large as possible. At the same time, considering about the wearing comfort and miniaturization of a wearable electronic, especially collection of 32 leads or 64 leads of EEG signals, the electrode should not be too large. In the implementation process, the size of the electrode has been designed and tested in various ways. In order to ensure that the resistance of the textile electrode is less than 10KΩ at 10 Hz (where the effect of bioelectrical signal collection of the electrode is almost identical to that of a conventional wet electrode), the thickness of the conductive foam is kept between 3 mm and 8 mm, and the cross-sectional area of the textile electrode body is kept between 100 mm² and 1600 mm². For example, the textile electrode body may be made by a conductive foam with a length and a width of 10 mm×10 mm-40 mm×40 mm. When designing the electrode, the electrode cross-sectional area can be determined based on the measured resistance.

Figure 3:
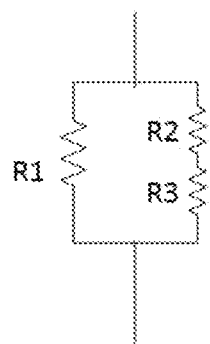
FIG. 3 is an equivalent circuit diagram of an electrode of the present invention.

FIG. 3 is an equivalent circuit diagram of the electrode of the present invention, the resistance of the conductive foam is about $10^5$ Ω·m. The cloth of the sweat absorbing layer can be an insulating material, and the resistance of the metal plating or the layer of conductive material on the conductive fabric is $10^{-6}$-$10^{-8}$ Ω·m. The resistance of the conductive fabric is significantly lower than that of the conductive foam and the sweat absorbing layer. In the structure of the present invention, the conductive fabric can be treated as a resistor having a resistance of R1, the conductive foam and the sweat absorbing layer fabric can be treated as two resistors in series, that is, R2 and R3, and the conductive fabric and the conductive foam can be treated as two resistors in parallel as shown in FIG. 3. When the surface area of the conductive fabric is large, the resistance of the textile electrode mainly depends on the resistance of the conductive fabric.

Providing through holes on the conductive fabric on the side in contact with the skin reduces the surface area of the conductive fabric on this side and increases the resistance of the entire conductive fabric, thereby increasing the resistance and reducing the conductivity of the textile electrode. When the resistance is too large, it will seriously affect the collection of bioelectrical signals. Therefore, the number and size of the through holes should be limited, and different sizes and numbers of through holes can be disposed depending on the surface area of the electrode. When the thickness of the electrode is constant, and the skin-electrode contact resistance of the electrode at 10 Hz is less than 10 KΩ, the total area of the through holes (e.g., the sum of the areas of several small through holes, or the area of a single large through hole) should be 30%-70% of the surface area of the conductive fabric on this side, that is, the total area of the through holes is 30%-70% of the cross-sectional area of the textile electrode body.

The specific embodiments of the present invention have been described above. It should be understood that the present invention is not limited to the specific embodiments described above, and various modifications and changes may be made by those skilled in the art without departing from the spirit of the disclosure, and are all within the scope of the disclosure as defined by the appended claims.

The invention claimed is:

1. A sweat absorbing textile electrode, comprising a textile electrode body and an electrical coupling member, the textile electrode body comprising a conductive foam and a conductive fabric wrapped around the conductive foam, the electrical coupling member being fixed on the conductive fabric; wherein a through hole is provided on the conductive fabric on a side in contact with a human skin; wherein a conductive cloth having a weaving density lower than that of the conductive fabric is disposed on the through hole.

2. The sweat absorbing textile electrode according to claim 1, wherein the textile electrode body further comprises a sweat absorbing layer between the conductive foam and the conductive fabric.

3. The sweat absorbing textile electrode according to claim 1, wherein the conductive foam has a thickness of 3 mm-8 mm, and the textile electrode body has a cross-sectional area of 100 mm²-1600 mm².

4. The sweat absorbing textile electrode according to claim 1, wherein the length and the width of said conductive foam are 10 mm×10 mm-40 mm×40 mm.

5. The sweat absorbing textile electrode according to claim 1, wherein an adhesive layer is provided on the inner surface of the conductive fabric for bonding; and the electrical coupling member is a metal conductive snap.

6. The sweat absorbing textile electrode according to claim 1, wherein the conductive fabric is formed by plating a metal-based material or coating a layer of conductive material on a cloth.

7. The sweat absorbing textile electrode according to claim 6, wherein the metal-based material is gold, silver, nickel or copper; and the conductive material is graphene or PEDOT.

8. The sweat absorbing textile electrode according to claim 6, wherein the resistance of the conductive foam is $10^5$ $\Omega \cdot m$, and the resistance of the metal plating or the layer of conductive material of the conductive fabric is $10^{-6}$-$10^{-8}$ $\Omega \cdot m$.

9. The sweat absorbing textile electrode according to claim 1, wherein the total area of said through hole is 30%-70% of the cross-sectional area of the textile electrode body.

\* \* \* \* \*